United States Patent [19]

Anderson

[11] Patent Number: 4,562,835

[45] Date of Patent: Jan. 7, 1986

[54] STREAMLINED T-SHAPED INTRAUTERINE DEVICE

[75] Inventor: Gregory K. Anderson, Scarborough, Canada

[73] Assignee: Ortho Pharmaceutical (Canada) Ltd., Don Mills, Canada

[21] Appl. No.: 573,080

[22] Filed: Jan. 23, 1984

[51] Int. Cl.⁴ .............................................. A61F 5/46
[52] U.S. Cl. .................................... 128/130; 128/127
[58] Field of Search ................................ 128/130, 127

[56] References Cited

U.S. PATENT DOCUMENTS

| | | | |
|---|---|---|---|
| 3,935,860 | 2/1976 | Hoff | 128/130 |
| 3,973,560 | 8/1976 | Emmett | 128/130 |
| 4,353,363 | 10/1982 | Quesada | 128/130 |

Primary Examiner—Gene Mancene
Assistant Examiner—C. W. Shedd
Attorney, Agent, or Firm—David J. Levy

[57] ABSTRACT

An intrauterine contraceptive device of a Tatum T shape which carries copper sleeves on its arms wherein the arm portion carrying the sleeve is of a smaller diameter than the remaining portion of the arm. This arrangement allows for minimization or elimination of an exposed and elevated copper sleeve edge which may abrade the uterus on insertion and/or removal.

7 Claims, 8 Drawing Figures

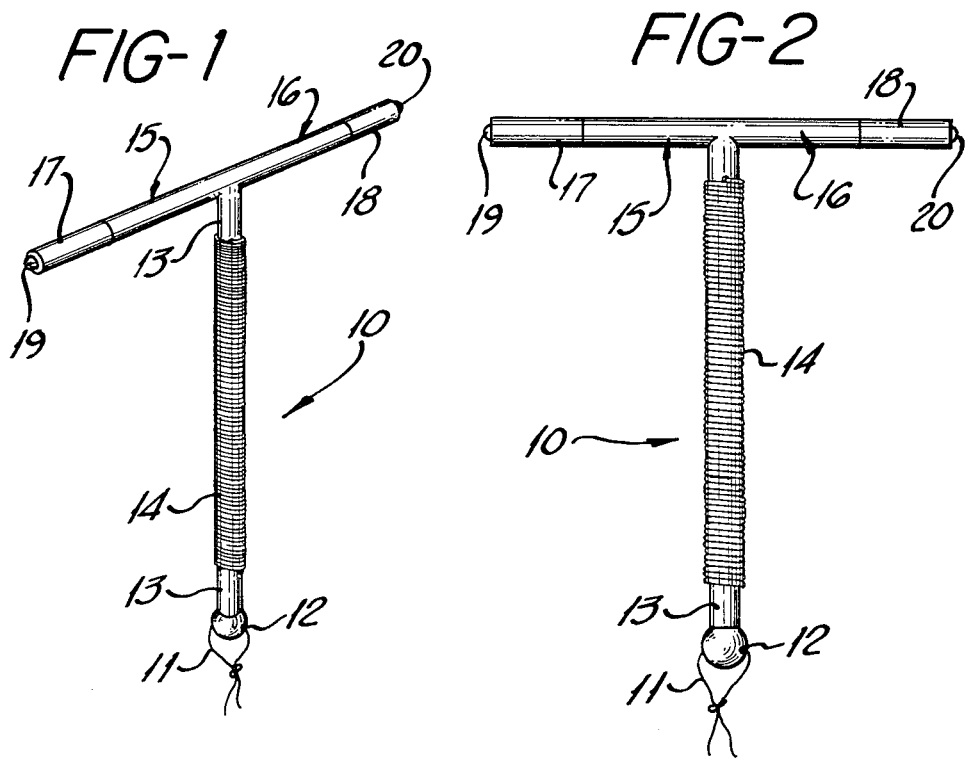
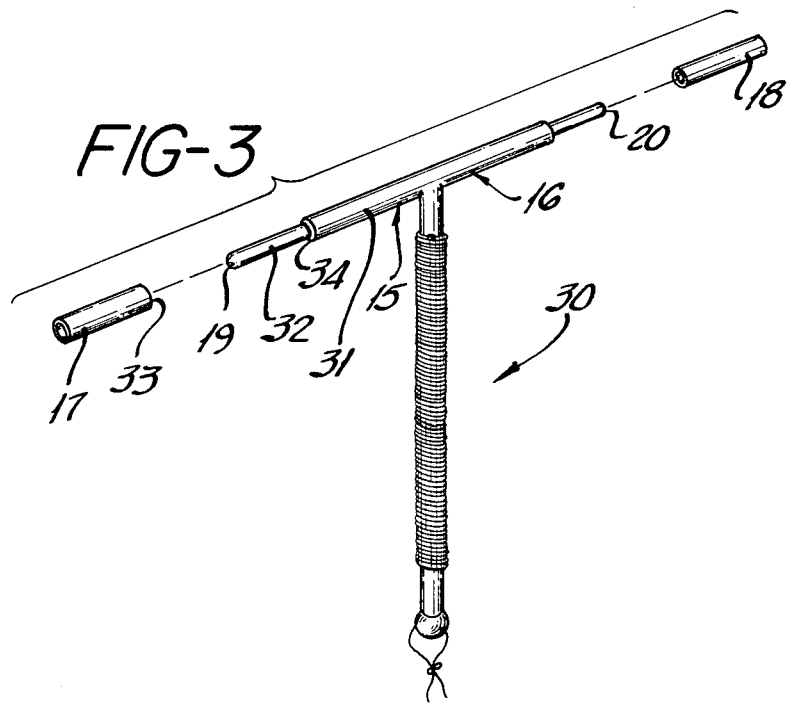

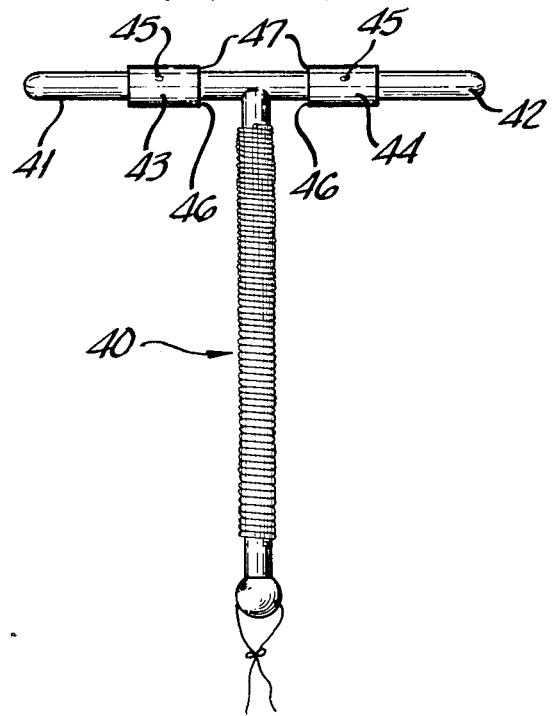

STREAMLINED T-SHAPED INTRAUTERINE DEVICE

The present invention comprises an improved intrauterine device (IUD) and a method for its use.

BACKGROUND OF THE INVENTION

IUD's having a T-shape, and generally known as a Tatum T, are disclosed in U.S. Pat. Nos. 3,533,406; 3,888,975; 3,898,986; 3,902,483; 3,935,860; 3,971,367; 3,993,057; 3,993,058; 4,198,966; 4,326,511; and 4,381,001. In addition, the use of copper windings on IUD's is known as seen by a reading of U.S. Pat. No. 3,563,235 and 3,711,035. However, the applicant has noted that copper, particularly in the form of copper sleeves may irritate the cervix as it is inserted or withdrawn through the cervical os.

It is an object of the invention to provide an IUD carrying copper sleeve tubing which is non-abrading to the uterus as it is placed in the uterus or removed.

SUMMARY OF THE INVENTION

A T-shaped IUD is provided with arms having a first portion of a given diameter and a second portion of a lesser diameter. Surrounding and tightly fitted to the second portion are lengths of copper tubing or sleeves. Preferably, the tubing is flush with the first portion so as to render the arms smooth to the touch.

BRIEF DESCRIPTION OF THE DRAWINGS

FIG. 1 is a perspective view of an IUD of the invention with copper sleeves attached to the ends of the IUD arms.

FIG. 2 is an elevational view of the IUD of FIG. 1.

FIG. 3 is an exploded perspective view of the IUD of FIG. 1 with the copper sleeves pulled away from the IUD.

FIG. 4 is an elevational view of an IUD of the prior art.

DETAILED DESCRIPTION OF THE INVENTION

Figure 5:
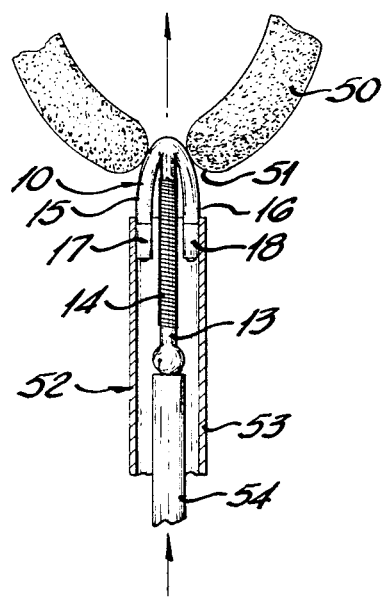
FIG. 5 is a schematic view showing an IUD of the present invention being inserted into the uterus through the cervical os with an IUD inserter.

The T-shaped IUD of the invention comprises a stem portion, a left arm and a right arm, each of said stem and arms having essentially a circular cross section. As is apparent from the drawings, the cross section can be somewhat eliptical as long as sharp edges, e.g., as in a triangular cross section, are avoided. Each of the arms comprise a first portion (i) which is usually of a diameter which is approximately equal to the diameter of the stem. A second portion (ii) in each arm is provided which has a diameter smaller than that of the first portion and carried on the second portion is a length of copper tubing. Preferably, the copper tubing is disposed along about $\frac{1}{4}$ to $\frac{1}{2}$ of the length of each of the arms. Preferably, the two portions are in the form of coaxial solid cylinders.

The second portion of each arm having a smaller diameter than the first portion can be located at the arm portion directly adjacent to the stem, between the stem and the terminus of the arm or at the terminus of the arm. Preferably, the second portion of each of said arms of a smaller diameter is located at the terminus of each arm. Location of the second or narrower portion of each arm at the terminus allows one to pass the length of copper tubing directly onto the arm. If the narrow portion of the arm is located adjacent to the stem or between the terminus and the stem, one may slit the copper tube lengthwise, open it and then close it over the narrow portion of the arm. Alternatively, the copper sleeve can be heated so as to expand the inside diameter thereof and pass it over a first or wider portion of the arm at the terminus and onto the narrow portion of the arm. Upon cooling of the sleeve, it will return to its original narrower cross section around the second portion of the arm having a smaller diameter. A third alternative is to place the copper sleeves in the mold for the IUD and introduce the plastic from which the IUD is constructed into the mold so as to affix the sleeves during molding. Preferably, the copper tubing is affixed to the arm with a small crimp in the tubing, although physiologically-compatible glues may be used.

The outside diameter of the copper tubing used in the IUD of the present invention is preferably equal to the diameter of the first portion of each of the arms so as to render the arms entirely flush. In addition, if the second portion of each of the arms is located at the terminus of the arm, the second portion is preferably slightly longer than the length of copper tubing utilized. This allows a small, rounded portion of the IUD arm to extend beyond the copper tubing and prevents the edge of the copper tubing from abrading the inside of the uterus. The inside diameter of the tubing is slightly larger than the diameter of the second portion (ii) of the arm to allow a tight frictional fit and prevent the tubing from slipping off of the arm.

Preferably, the copper tubing is carried on the IUD arm so as to abut the portion of larger diameter without allowing a cavity or opening between the edge of the copper tubing and the end of the first portion of the arm having a larger diameter.

The present invention will be more completely understood by reference to the drawings. In FIG. 1, an IUD 10 of the present invention is shown with a tail 11 of a monofilament string attached to the IUD through a hole 12 in a rounded end portion of the stem 13 of the IUD. Also carried on the stem 13 is a helical winding 14 of copper wire, also used for contraception. At one end of the stem 13 are attached left arm 15 and right arm 16 of the IUD. Preferably, as explained hereafter, the IUD is constructed of a flexible polymeric material as known in the art. Carried on arms 15 and 16 are lengths of copper tubing or sleeves 17 and 18. Projecting from copper tubings 17 and 18 are projecting portions of 19 and 20 of arms 15 and 16.

FIG. 2 is an elevational view of the IUD 10 of FIG. 1.

FIG. 3 is an exploded perspective view of an IUD 30 of the present invention. This view details the construction of the arm 15 shown in FIG. 1. Arm 15 comprises a first portion 31 of a diameter approximately equal to the diameter of the stem. A second portion 32 is provided with a smaller diameter than that of the first portion 31 terminating in the rounded end portion 19. Preferably, copper sleeve 17 is inserted over the second portion 32 of the arm 15 with the abutment of the end 33 against the wall 34 of arm 15. Wall 34 of arm 15 is formed by the change in diameter between portions 31 and 32.

FIG. 4 is an elevational view of an IUD 40 of the prior art, in particular the Copper T 380A described at page 45 of "An Atlas of Intrauterine Contraception" by Russel J. Thomsen, Hemisphere Publishing Corp. (1982). Referring to the portions of the IUD which distinguish from the present invention, the IUD 40 comprises a left arm 41 and a right arm 42 each carrying copper sleeves 43 and 44, respectively. Also shown is a crimp 45 which holds the copper sleeve in place on the arm. Copper sleeve 44 is shown to have a lower edge 46 and an upper edge 47 which are formed from the thickness of copper tubing. As can be seen from FIG. 4, when the arms 41 and 42 have a single constant diameter, the copper sleeves 43 and 44 must extend outward from the surface of the arms 41 and 42. When inserted into the uterus through the cervical os, arms 41 and 42 fold back toward the stem of the IUD and the edge 47 may scrape against the uterine tissue. Likewise, when withdrawn from the uterus, the arms 41 and 42 are bent upwards and edge 46 may also abrade the uterine tissue. The same is, of course, true of the edges of the copper sleeve 43.

FIG. 5 shows the insertion of an IUD 10 of the invention into the uterus 50 through the cervical os 51 by means of an IUD inserter 52 comprising an insertion tube 53 and a plunger 54. The smooth mounting of copper sleeves 17 and 18 allows a facile movement through the cervical os 51.

Figure 5A:
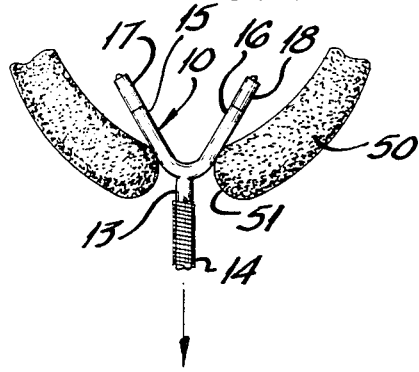
FIG. 5A is a schematic view of the IUD being withdrawn from the uterus.

FIG. 5A depicts extraction an IUD 10 of the present invention after insertion as shown in FIG. 5. As can be seen, the flush mounting of copper sleeves 17 and 18 allows for a smooth passage of the IUD out of the cervical os 51.

Figure 6:
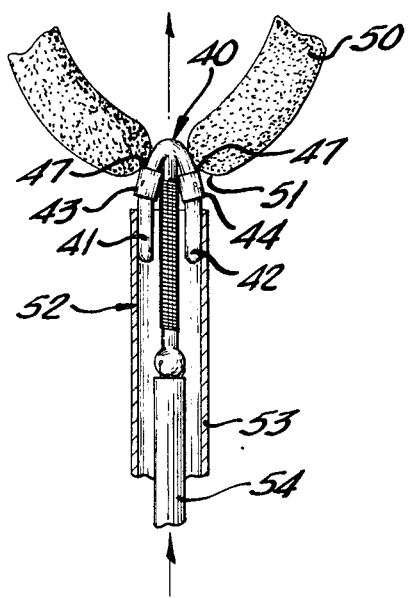
FIG. 6 is a schematic view of the prior art IUD of FIG. 4 being inserted into the cervical os with abrasion of the other edge of the cervical os.

FIG. 6 shows the insertion of an IUD 40 of the prior art, shown in more detail in FIG. 4, into the uterus 50 through the cervical os 51 of a patient. The insertion is shown using the IUD inserter 52 depicted in FIG. 5.

Copper sleeves 43 and 44 possess edge portions 47 which will cause abrasion during insertion which is not present in the IUD of the invention.

Figure 6A:
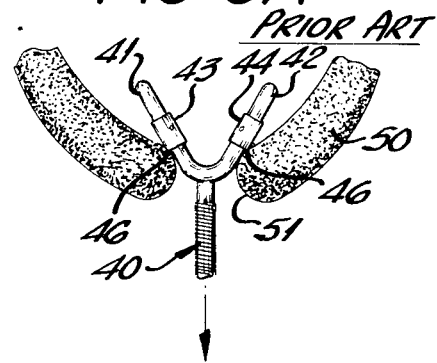
FIG. 6A is a schematic view of the IUD being withdrawn from the uterus with scraping of the uterine wall.

FIG. 6A depicts the extraction of an IUD 40 of the prior art after insertion as shown in FIG. 6, from the uterus 50 through the cervical os 51 of a patient. It can be seen from FIG. 6A that copper sleeves 43 and 44 will tend to abrade or scratch the uterine tissue in view of the presence of the edge 46 of the sleeve 44.

I claim:

1. A T-shaped intrauterine contraceptive device comprising a stem, a left arm and a right arm, each of said stem and arms having an essentially circular cross-section, wherein the arms each comprise:
    a first portion; and
    a second portion which has a diameter smaller than the first portion and is located at the terminus of the arm; and
    a length of copper tubing disposed on the second portion of each of said arms and attached thereto, the outside diameter of said copper tubing being equal to the outside diameter of said first portion of each of said arms.

2. The device of claim 1, wherein the diameter of said first portion is approximately equal to the diameter of the stem.

3. The device of claim 1, wherein said length of copper tubing is disposed along about ¼ to ½ of the length of each of said arms.

4. The device of claim 1, wherein said length of copper tubing is affixed to said arm with a crimp in said tubing.

5. The device of claim 1, wherein said second portion of each of said arms is slightly longer than the length of copper tubing.

6. The device of claim 5, wherein the length of copper tubing abuts the first portion of each of said arms.

7. The device of claim 1, wherein said device further comprises a length of copper wire wound helically around said stem.

* * * * *